(12) United States Patent
Do et al.

(10) Patent No.: US 9,359,388 B2
(45) Date of Patent: Jun. 7, 2016

(54) TRANSITION METAL COMPOUND HAVING HETEROATOM, CATALYTIC COMPOSITION INCLUDING THE SAME, AND METHOD FOR PREPARING POLYMERS USING THE SAME

(71) Applicant: LG CHEM, LTD., Seoul (KR)

(72) Inventors: Young Shil Do, Daejeon (KR); Yoon Hee Cho, Daejeon (KR); Choong Hoon Lee, Daejeon (KR); Seung Hwan Jung, Daejeon (KR); Don Ho Kum, Daejeon (KR); Sang Eun Park, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 14/439,159

(22) PCT Filed: Oct. 16, 2014

(86) PCT No.: PCT/KR2014/009753
§ 371 (c)(1),
(2) Date: Apr. 28, 2015

(87) PCT Pub. No.: WO2015/057001
PCT Pub. Date: Apr. 23, 2015

(65) Prior Publication Data
US 2015/0239916 A1 Aug. 27, 2015

(30) Foreign Application Priority Data
Oct. 16, 2013 (KR) .................. 10-2013-0123476

(51) Int. Cl.
| | | |
|---|---|---|
| C07F 17/00 | (2006.01) | |
| C08F 4/6592 | (2006.01) | |
| C08F 10/00 | (2006.01) | |
| C07F 7/28 | (2006.01) | |
| C08F 4/76 | (2006.01) | |
| B01J 31/14 | (2006.01) | |
| B01J 31/18 | (2006.01) | |
| B01J 31/22 | (2006.01) | |
| C08F 210/16 | (2006.01) | |
| C08F 4/659 | (2006.01) | |

(52) U.S. Cl.
CPC . *C07F 7/28* (2013.01); *B01J 31/14* (2013.01); *B01J 31/1805* (2013.01); *B01J 31/2295* (2013.01); *C07F 17/00* (2013.01); *C08F 4/6592* (2013.01); *C08F 4/76* (2013.01); *C08F 210/16* (2013.01); *B01J 2231/12* (2013.01); *B01J 2531/40* (2013.01); *B01J 2531/46* (2013.01); *B01J 2531/48* (2013.01); *B01J 2531/49* (2013.01); *C08F 4/65904* (2013.01); *C08F 4/65908* (2013.01); *C08F 4/65912* (2013.01); *C08F 4/65916* (2013.01); *C08F 2420/02* (2013.01); *C08F 2420/06* (2013.01); *Y02P 20/52* (2015.11)

(58) Field of Classification Search
CPC .... C07F 17/00; C08F 4/6592; C08F 4/65908; C08F 4/65912
See application file for complete search history.

(56) References Cited

U.S. PATENT DOCUMENTS

| | | | |
|---|---|---|---|
| 5,064,802 | A | 11/1991 | Stevens et al. |
| 6,548,686 | B2 | 4/2003 | Nabika et al. |
| 2007/0225158 | A1 | 9/2007 | Lee et al. |
| 2008/0026792 | A1 | 1/2008 | Son |
| 2010/0179291 | A1 | 7/2010 | Lee et al. |
| 2011/0152529 | A1 | 6/2011 | Lee et al. |
| 2011/0160413 | A1 | 6/2011 | Lee et al. |
| 2013/0203949 | A1 | 8/2013 | Lee et al. |
| 2013/0211020 | A1 | 8/2013 | Lee et al. |
| 2013/0211021 | A1 | 8/2013 | Lee et al. |
| 2013/0211023 | A1 | 8/2013 | Lee |
| 2013/0211024 | A1 | 8/2013 | Lee et al. |
| 2013/0317186 | A1 | 11/2013 | Lee et al. |
| 2013/0317187 | A1 | 11/2013 | Lee et al. |

FOREIGN PATENT DOCUMENTS

| | | |
|---|---|---|
| JP | 2003-201308 A | 7/2003 |
| KR | 10-0820542 B1 | 4/2008 |
| KR | 10-2008-0101542 A | 11/2008 |
| KR | 10-0986301 B1 | 10/2010 |
| WO | WO 2008/140280 A2 | 11/2008 |

OTHER PUBLICATIONS

Chen et al., "A Novel Phenolate "Constrained Geometry" Catalyst System. Efficient Synthesis, Structural Characterization, and α-Olefin Polymerization Catalysts", vol. 16, pp. 5958-5963, Organometallics 1997.

Christie et al., "Novel Routes to Bidentate Cyclopentadienyl-Alkoxide Complexes of Titanium: Synthesis of (η5-σ-C5R14CHR2CH2CR3R4O)TiCl2", vol. 18, pp. 348-359, Organometallics 1999.

(Continued)

*Primary Examiner* — Caixia Lu
(74) *Attorney, Agent, or Firm* — Birch, Stewart, Kolasch & Birch, LLP

(57) ABSTRACT

The present invention discloses a transition metal compound having a novel structure and including a heteroatom, a catalyst composition including the same, and a method for preparing polymers using the same. The transition metal compound according to an embodiment of the present invention has good copolymerization properties, and a polymer having a low density may be prepared using thereof. Thus, a copolymer having various uses may be prepared.

17 Claims, No Drawings

(56) References Cited

OTHER PUBLICATIONS

Gibson et al., "Advances in Non-Metallocene Olefin Polymerization Catalysis", vol. 103, pp. 283-315, Chem. Rev. 2003.

Gielens et al., "Titanium Hydrocarbyl Complexes with a Linked Cyclopentadienyl-Alkoxide Ancillary Ligand; Participation of the Ligand in an Unusual Activation of a (Trimethylsilyl)methyl Group", vol. 17, pp. 1652-1654, Organometallics 1998.

International Search Report issued in PCT/KR2014/009753 dated Dec. 23, 2014.

Kim et al., "Preparation of Thiophene-Fused and Tetrahydroquinoline-Linked Cyclopentadienyl Titanium Complexes for Ethylene/α-Olefin Copolymerization", vol. 3, pp. 104-124, Catalysts 2013.

Rau et al., "Synthesis and application in high-pressure polymerization of a titanium complex with a linked cyclopentadienyl-phenoxide ligand", vol. 608, pp. 71-75, Journal of Organometallic Chemistry (2000).

Turner et al., "Facile resolution of constrained geometry indenyl-phenoxide ligation", pp. 1034-1035, Chem. Commun., 2003.

Written Opinion of the International Searching Authority issued in PCT/KR2014/009753 dated Dec. 23, 2014.

Zhang et al., "Constrained Geometry Tetramethylcyclopentadienyl-phenoxytitanium Dichlorides: Template Synthesis, Structures, and Catalytic Properties for Ethylene Polymerization", vol. 23, pp. 540-546, Organometallics 2004.

Extended European Search Report for European Application No. 14853389.6, dated Oct. 20, 2015.

Park et al., "Preparation of half-metallocenes of thiophene-fused and tetrahydroquinoline-linked cyclopentadienyl ligands for ethylene/α-olefin copolymerization," Dalton Transactions, vol. 39, Sep. 21, 2010, pp. 9994-10002.

Ryabov et al., "Constrained geometry complexes of titanium (IV) and zirconium (IV) involving cyclopentadienyl fused to thiophene ring," Journal of Organometallic Chemistry, vol. 690, 2005 (Available online Aug. 5, 2005), pp. 4213-4221.

Ryabov et al., "Zirconium Complexes with Cyclopentadienyl Ligands Involving Fused a Thiophene Fragment," Organometallics, vol. 21, No. 14, 2002 (Publication on Web Jun. 8, 2002), pp. 2842-2855, XP-001106373.

TRANSITION METAL COMPOUND HAVING HETEROATOM, CATALYTIC COMPOSITION INCLUDING THE SAME, AND METHOD FOR PREPARING POLYMERS USING THE SAME

TECHNICAL FIELD

The present invention relates to a transition metal compound having a novel structure, a catalyst composition including the same and a method for preparing polymers using the same. More particularly, the present invention relates to a transition metal compound including a heteroatom and having a novel structure, a catalyst composition including the same and a preparation method of a polymer using the catalyst composition.

BACKGROUND ART

[Me$_2$Si(Me$_4$C$_5$)NtBu]TiCl$_2$ (Constrained-Geometry Catalyst, hereinafter, will be abbreviated as CGC) was reported by Dow Co. in the early 1990s (U.S. Pat. No. 5,064,802), and excellent aspects of the CGC in the copolymerization reaction of ethylene and alpha-olefin may be summarized in the following two points when compared to commonly known metallocene catalysts: (1) At a high polymerization temperature, high activity is shown and a polymer having high molecular weight is produced, and (2) the copolymerization degree of alpha-olefin having large steric hindrance such as 1-hexene and 1-octene is excellent. In addition, as various properties of the CGC during performing a polymerization reaction are gradually known, efforts of synthesizing the derivatives thereof and using as a polymerization catalyst has been actively conducted in academy and industry As one approach, the synthesis of a metal compound introducing various bridges instead of a silicon bridge and a nitrogen substituent and the polymerization thereof has been conducted. Typical metal compounds known until now are illustrated as the following Compounds (1) to (4) (Chem. Rev. 2003, 103, 283).

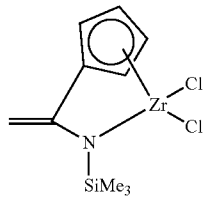

(1)

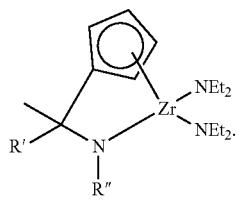

(2)

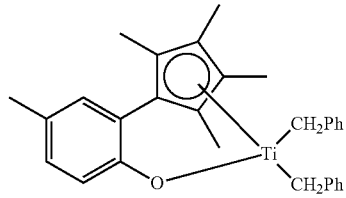

(3)

(4)

The above Compounds (1) to (4) introduce a phosphorous bridge (1), an ethylene or a propylene bridge (2), a methylidene bridge (3) or a methylene bridge (4), each independently, instead of the silicon bridge of a CGC structure. However, improved results on activity, copolymerization performance, etc. could not be obtained by applying an ethylene polymerization or a copolymerization with alpha-olefin when compared to those obtained by applying the CGC.

As another approach, a compound composed of an oxido ligand instead of the amido ligand of the CGC has been synthesized a lot, and an attempt on the polymerization using thereof has been conducted to some extent. Examples thereof are summarized in the following.

(5)

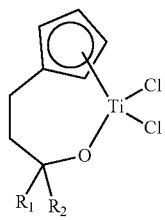

(6)

(7)

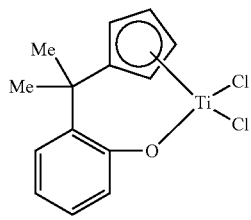

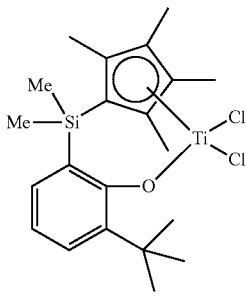

Compound (5) has been reported by T. J. Marks et al. and is characterized in that a cyclopentadiene (Cp) derivative and an oxido ligand are bridged via an ortho-phenylene group (Organometallics 1997, 16, 5958). A compound having the same bridged group and a polymerization using thereof have been reported by Mu et al. (Organometallics 2004, 23, 540). In addition, the bridging of an indenyl ligand and an oxido ligand by the same ortho-phenylene group has been reported by Rothwell et al. (Chem. Commun. 2003, 1034). Compound (6) has been reported by Whitby et al. and is characterized in that a cyclopentadienyl ligand and an oxido ligand are bridged by three carbon atoms (Organometallics 1999, 18, 348). The above catalysts have been reported to show activity in a syndiotactic polystyrene polymerization. Similar compounds have been also reported by Hessen et al. (Organometallics 1998, 17, 1652). Compound (7) has been reported by Rau et al. and is characterized in showing activity in an ethylene polymerization and an ethylene/1-hexene copolymerization at a high temperature and high pressure (210° C., 150 MPa) (J. Organomet. Chem. 2000, 608, 71). In addition, the synthesis of a catalyst (8) having similar structure as that of Compound (7) and a polymerization using the same at high temperature and high pressure have been filed by Sumitomo Co. (U.S. Pat. No. 6,548,686). However, not many catalysts among the above attempts are practically applied in commercial plants. Accordingly, a catalyst showing further improved polymerization performance is required, and a simple preparation method of the catalysts is required.

PRIOR ART DOCUMENTS

Patent Documents

U.S. Pat. No. 5,064,802
U.S. Pat. No. 6,548,686

Non-Patent Documents

Chem. Rev. 2003, 103, 283
Organometallics 1997, 16, 5958
Organometallics 2004, 23, 540
Chem. Commun. 2003, 1034
Organometallics 1999, 18, 348
Organometallics 1998, 17, 1652
J. Organomet. Chem. 2000, 608, 71

DISCLOSURE OF THE INVENTION

Technical Problem

In the present invention, a transition metal compound including a heteroatom and having a novel structure, a catalyst composition including the same and a preparation method of a polymer using the catalyst composition are described.

Technical Solution

According to an aspect of the present invention, there is provided a transition metal compound of Chemical Formula 1 below:

[Chemical Formula 1]

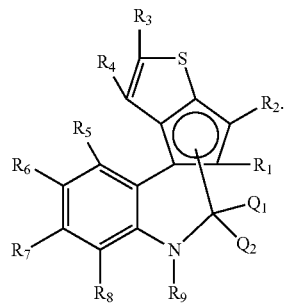

In the above Chemical Formula 1,

M is a transition metal in group 4, $Q_1$ and $Q_2$ are the same or different and each independently hydrogen; halogen; alkyl having 1 to 20 carbon atoms; alkenyl having 2 to 20 carbon atoms; aryl having 6 to carbon atoms; alkylaryl having 6 to 20 carbon atoms; arylalkyl having 7 to 20 carbon atoms; alkylamido having 1 to 20 carbon atoms; arylamido having 6 to 20 carbon atoms; or alkylidene having 1 to 20 carbon atoms, $R_1$ to $R_4$ are the same or different and each independently hydrogen; silyl; alkyl having 1 to 20 carbon atoms; alkenyl having 2 to 20 carbon atoms; aryl having 6 to carbon atoms; alkylaryl having 7 to 20 carbon atoms; arylalkyl having 7 to 20 carbon atoms; a metalloid radical of a metal in group 14, substituted with hydrocarbyl having 1 to 20 carbon atoms; $R_1$ and $R_2$ may be connected to each other, or $R_3$ and $R_4$ may be connected to each other to form an aliphatic ring having 5 to 20 carbon atoms or an aromatic ring having 6 to 20 carbon atoms; the aliphatic ring or the aromatic ring may be substituted with halogen, alkyl having 1 to 20 carbon atoms, alkenyl having 2 to 20 carbon atoms, or aryl having 6 to 20 carbon atoms, $R_5$ to $R_9$ are the same or different and each independently hydrogen; alkyl having 1 to 20 carbon atoms; alkenyl having 2 to 20 carbon atoms; aryl having 6 to 20 carbon atoms; alkylaryl having 7 to 20 carbon atoms; arylalkyl having 7 to 20 carbon atoms; at least two of $R_5$ to $R_9$ may be connected to each other to form an aliphatic ring having 5 to 20 carbon atoms or an aromatic ring having 6 to 20 carbon atoms; the aliphatic ring or the aromatic ring may be substituted with halogen, alkyl having 1 to 20 carbon atoms, alkenyl having 2 to 20 carbon atoms, or aryl having 6 to 20 carbon atoms.

According to another aspect of the present invention, there is provided a catalyst composition including the transition metal compound of the above Chemical Formula 1.

According to further another aspect of the present invention, there is provided a preparation method of a polymer using the catalyst composition.

Advantageous Effects

In the transition metal compound according to the present invention, an amido ligand and an ortho-phenylene form a condensed ring, and the position of the heteroatom of a thiophene introduced in a five-membered ring pi-ligand combined with the ortho-phenylene is controlled. Thus, the transition metal compound may be used as a catalyst having good copolymerization properties, and a polymer having a low density may be prepared by using thereof.

BEST MODE FOR CARRYING OUT THE INVENTION

According to an aspect of the present invention, a transition metal compound of the above-described Chemical Formula 1 is provided.

In the transition metal compound of Chemical Formula described in the present invention, a metal site is connected to a cyclopentadienyl ligand connected to a phenylene bridge introducing an amido group as a ring, and the structure thereof has a narrow Cp-M-N angle and a wide $Q_1$-M-$Q_2$ angle to which a monomer may approach. Thus, cyclopentadiene, a phenylene bridge, nitrogen and the metal site are connected in order, and more stable and rigid pentagonal ring structure may be formed. In addition, in the structure of the compound represented by the above Chemical Formula 1, thiophene is fused so that the sulfur (S) atom of a heterocycle is combined to position 3 of the cyclopentadiene, thereby increasing activity when used as a catalyst and markedly increasing the molecular weight of a polymer to be prepared. Accordingly, the transition metal compound of the above Chemical Formula 1 may play the role of a catalyst having good copolymerization properties and used for preparing a polymer having a low density.

In an embodiment, when applying the compounds for the polymerization of an olefin after reacting with a cocatalyst such as methyl aluminoxane or $B(C_6F_5)_3$ and activating, a polyolefin having high activity, high molecular weight and high copolymerization degree may be produced even at a high polymerization temperature. Particularly, since a large amount of an alpha-olefin may be introduced as well as a linear polyethylene having a low density of 0.910-0.930 g/cc due to the structural characteristics of the catalyst, a polyolefin copolymer having a low density of less than 0.91 g/cc may be produced. In particular, a polymer having narrow molecular weight distribution (MWD, hereinafter 'MWD') with respect to a constrained-geometry catalyst (CGC, hereinafter 'CGC'), good copolymerization properties and high molecular weight in a low density region may be prepared by using a catalyst composition including the transition metal compound. In addition, diverse substituents may be introduced in a cyclopentadienyl group fused with thiophene and quinolines, and electronic and steric environment around a metal may be easily controlled, and so, the structure and physical properties of the polyolefin thus produced may be controlled. The compound of the above Chemical Formula 1 may be preferably used for preparing a catalyst for polymerizing an olefin monomer, however the present invention is not limited thereto. The transition metal compound may be used in any other applicable fields.

In the present invention, alkyl and alkenyl may be a linear or branched chain alkyl or alkenyl.

In the present invention, silyl may be a substituted silyl with alkyl having 1 to 20 carbon atoms, for example, trimethylsilyl or triethylsilyl.

In the present invention, aryl includes a single ring aryl or a polyring aryl, for example, phenyl, naphthyl, anthryl, phenanthryl, crysenyl, pyrenyl, etc.

According to an embodiment of the present invention, $R_8$ and $R_9$ in the above Chemical Formula 1 are combined to each other to form a five-membered or six-membered aliphatic ring. The above Chemical Formula 1 may be represented by Chemical Formula 2 below:

[Chemical Formula 2]

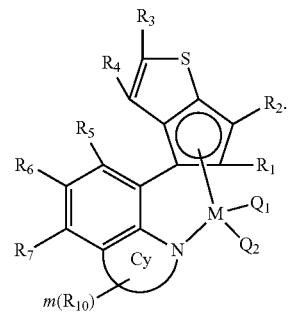

In the above Chemical Formula 2,

Cy is a five-membered or six-membered aliphatic ring, each $R_{10}$ is independently hydrogen; alkyl having 1 to 20 carbon atoms; alkenyl having 2 to 20 carbon atoms; aryl having 6 to 20 carbon atoms; alkylaryl having 7 to 20 carbon atoms; or arylalkyl having 7 to 20 carbon atoms, m is an integer from 1 to 4 when Cy is the five-membered aliphatic ring and an integer from 1 to 6 when Cy is the six-membered aliphatic ring, and the remaining substituents are the same as defined in Chemical Formula 1.

According to another aspect of the present invention, the above Chemical Formula 2 may be represented by the following Chemical Formula 3 or 4.

[Chemical Formula 3]

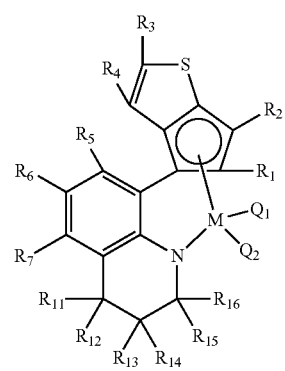

In the above Chemical Formula 3, $R_{11}$ to $R_{16}$ are each independently hydrogen; alkyl having 1 to 20 carbon atoms; alkenyl having 2 to 20 carbon atoms; aryl having 6 to 20 carbon atoms; alkylaryl having 7 to 20 carbon atoms; or arylalkyl having 7 to 20 carbon atoms, and the remaining substituents are the same as defined in Chemical Formula 1.

[Chemical Formula 4]

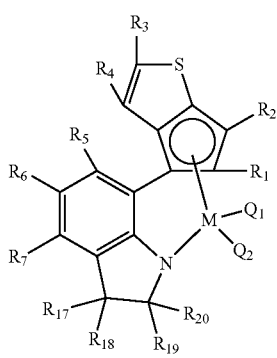

In the above Chemical Formula 4, $R_{17}$ to $R_{20}$ are each independently hydrogen; alkyl having 1 to 20 carbon atoms; alkenyl having 2 to 20 carbon atoms; aryl having 6 to 20 carbon atoms; alkylaryl having 7 to 20 carbon atoms; or arylalkyl having 7 to 20 carbon atoms, and the remaining substituents are the same as defined in Chemical Formula 1.

According to another aspect of the present invention, the above Chemical Formula 2 may be represented by the following Chemical Formula 5 or 6.

[Chemical Formula 5]

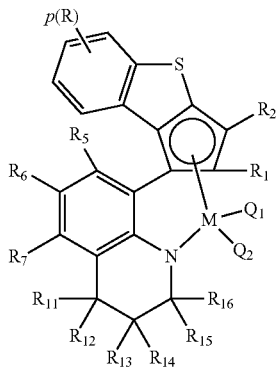

In the above Chemical Formula 5,

R and $R_{11}$ to $R_{15}$ are each independently hydrogen; alkyl having 1 to 20 carbon atoms; alkenyl having 2 to 20 carbon atoms; aryl having 6 to 20 carbon atoms; alkylaryl having 7 to 20 carbon atoms; or arylalkyl having 7 to 20 carbon atoms, p is an integer from 1 to 4, and the remaining substituents are the same as defined in Chemical Formula 1.

[Chemical Formula 6]

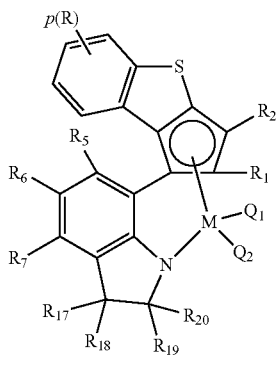

In the above Chemical Formula 6,

R and $R_{17}$ to $R_{20}$ are each independently hydrogen; alkyl having 1 to 20 carbon atoms; alkenyl having 2 to 20 carbon atoms; aryl having 6 to 20 carbon atoms; alkylaryl having 7 to 20 carbon atoms; or arylalkyl having 7 to 20 carbon atoms, p is an integer from 1 to 4, and the remaining substituents are the same as defined in Chemical Formula 1.

According to another aspect of the present invention, $R_1$ and $R_2$ are hydrogen or alkyl having 1 to 20 carbon atoms.

According to another aspect of the present invention, $R_1$ and $R_2$ are hydrogen or alkyl having 1 to 6 carbon atoms.

According to another aspect of the present invention, $R_1$ and $R_2$ are hydrogen or methyl.

According to another aspect of the present invention, at least one of $R_1$ and $R_2$ is alkyl having 1 to 20 carbon atoms.

According to another aspect of the present invention, $R_1$ is alkyl having 1 to 20 carbon atoms, and $R_2$ is hydrogen.

According to another aspect of the present invention, $R_1$ is alkyl having 1 to 6 carbon atoms, and $R_2$ is hydrogen.

According to another aspect of the present invention, $R_1$ is methyl, and $R_2$ is hydrogen.

According to another aspect of the present invention, $R_1$ and $R_2$ are alkyl having 1 to 20 carbon atoms.

According to another aspect of the present invention, $R_1$ and $R_2$ are alkyl having 1 to 6 carbon atoms.

According to another aspect of the present invention, $R_1$ and $R_2$ are methyl.

According to another aspect of the present invention, $R_3$ to $R_7$ are the same or different and each independently hydrogen; alkyl having 1 to 20 carbon atoms; or alkenyl having 2 to 20 carbon atoms.

According to another aspect of the present invention, $R_3$ to $R_7$ are the same or different and each independently hydrogen; or alkyl having 1 to 20 carbon atoms.

According to another aspect of the present invention, $R_3$ to $R_7$ are hydrogen.

According to another aspect of the present invention, $R_{11}$ to $R_{16}$ of the above Formula 3 are each independently hydrogen; alkyl having 1 to 20 carbon atoms; or alkenyl having 2 to 20 carbon atoms.

According to another aspect of the present invention, $R_{11}$ to $R_{16}$ of the above Chemical Formula 3 are each independently hydrogen; or alkyl having 1 to 20 carbon atoms.

According to another aspect of the present invention, at least one of $R_{11}$ to $R_{16}$ of the above Chemical Formula 3 is alkyl having 1 to 20 carbon atoms.

According to another aspect of the present invention, $R_{11}$ to $R_{15}$ are hydrogen, and $R_{16}$ is alkyl having 1 to 20 carbon atoms in the above Chemical Formula 3.

According to another aspect of the present invention, $R_{11}$ to $R_{15}$ are hydrogen, and $R_{16}$ is alkyl having 1 to 6 carbon atoms in the above Chemical Formula 3.

According to another aspect of the present invention, $R_{11}$ to $R_{15}$ are hydrogen, and $R_{16}$ is methyl in the above Chemical Formula 3.

According to another aspect of the present invention, $R_{11}$ to $R_{16}$ of the above Chemical Formula 3 are hydrogen.

According to another aspect of the present invention, $R_{17}$ to $R_{20}$ of the above Chemical Formula 4 are independently hydrogen; alkyl having 1 to 20 carbon atoms; or alkenyl having 2 to 20 carbon atoms.

According to another aspect of the present invention, $R_{17}$ to $R_{20}$ of the above Chemical Formula 4 are independently hydrogen; or alkyl having 1 to 20 carbon atoms.

According to another aspect of the present invention, at least one of $R_{17}$ to $R_{20}$ of the above Chemical Formula 4 is alkyl having 1 to 20 carbon atoms.

According to another aspect of the present invention, $R_{17}$ to $R_{19}$ are hydrogen, and $R_{20}$ is alkyl having 1 to 20 carbon atoms in the above Chemical Formula 4.

According to another aspect of the present invention, $R_{17}$ to $R_{19}$ are hydrogen, and $R_{20}$ is alkyl having 1 to 6 carbon atoms in the above Chemical Formula 4.

According to another aspect of the present invention, $R_{17}$ to $R_{19}$ are hydrogen, and $R_{20}$ is methyl in the above Chemical Formula 4.

According to another aspect of the present invention, $R_{17}$ to $R_{20}$ of the above Chemical Formula 4 are hydrogen.

According to another aspect of the present invention, M is Ti, Hf or Zr.

According to another aspect of the present invention, M is Ti.

According to another aspect of the present invention, $Q_1$ and $Q_2$ are each independently halogen.

According to another aspect of the present invention, $Q_1$ and $Q_2$ are Cl.

According to another aspect of the present invention, $R_1$, $R_2$ and $R_{11}$ to $R_{16}$ are hydrogen or alkyl having 1 to 6 carbon atoms in the above Chemical Formula 3 or 5.

According to another aspect of the present invention, $R_1$ and $R_2$ are alkyl having 1 to 6 carbon atoms, and $R_{11}$ to $R_{16}$ are hydrogen in the above Chemical Formula 3 or 5.

According to another aspect of the present invention, $R_1$ and $R_{16}$ are alkyl having 1 to 6 carbon atoms, $R_2$ is hydrogen or alkyl having 1 to 6 carbon atoms, and $R_{11}$ to $R_{15}$ are hydrogen in the above Chemical Formula 3 or 5.

According to another aspect of the present invention, $R_1$, $R_2$ and $R_{17}$ to $R_{20}$ are hydrogen or alkyl having 1 to 6 carbon atoms in the above Chemical Formula 4 or 6.

According to another aspect of the present invention, $R_1$ and $R_2$ are alkyl having 1 to 6 carbon atoms, and $R_{17}$ to $R_{20}$ are hydrogen in the above Chemical Formula 4 or 6.

According to another aspect of the present invention, $R_1$ and $R_{20}$ are alkyl having 1 to 6 carbon atoms, $R_2$ is hydrogen or alkyl having 1 to 6 carbon atoms, and $R_{17}$ to $R_{19}$ are hydrogen in the above Chemical Formula 4 or 6.

According to another aspect of the present invention, the compound of the above Chemical Formula 1 is selected from compounds represented by the following Chemical Formulae.

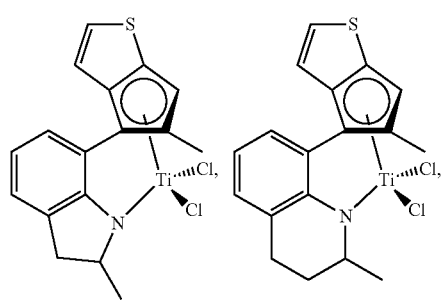

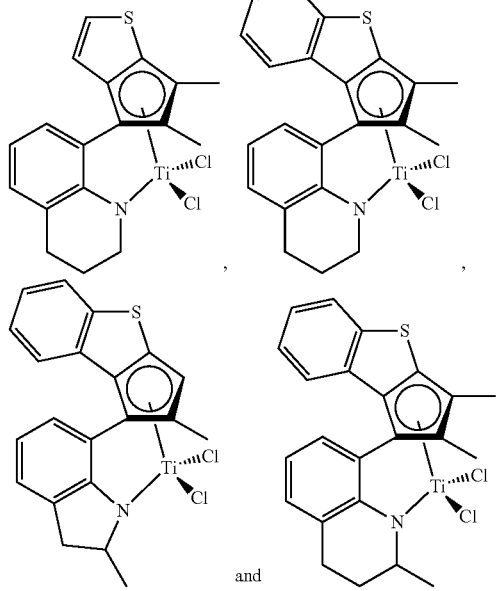

The compound of the above Chemical Formula 1 may be prepared by the following reaction.

[Reaction 1]

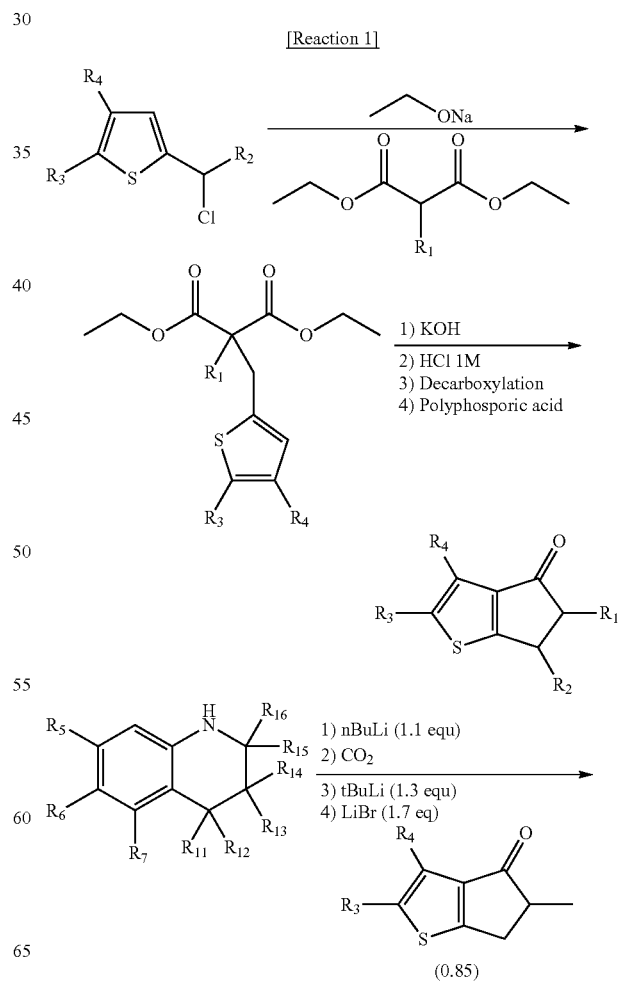

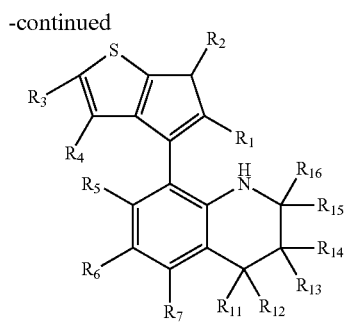

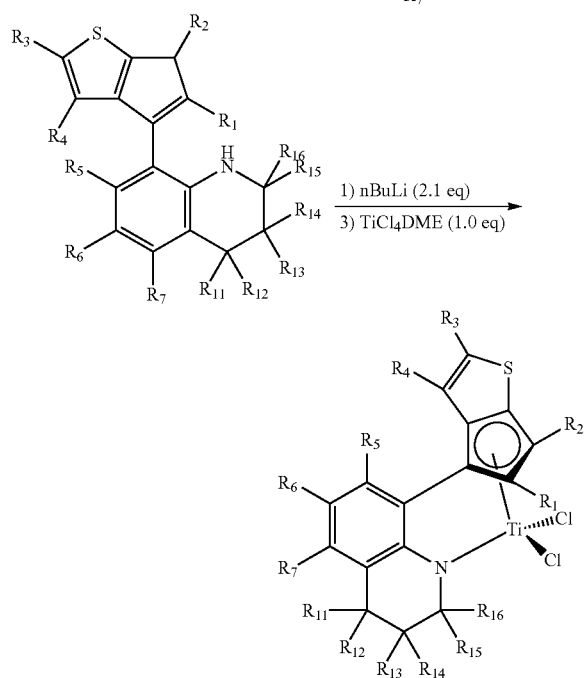

In the above Reaction 1, the substituents are the same as defined in the above Chemical Formula 3.

The substituent of a target compound may be changed by changing starting materials and reactants used in the above reaction. In addition, tetrahydroquinoline was used in the above Reaction 1, however, a compound of Chemical Formula 4 may be prepared by using indoline instead of the tetrahydroquinoline.

In the present invention, a catalyst composition including a compound of the above Chemical Formula 1 is provided.

The catalyst composition may further include a cocatalyst. As the cocatalyst, known materials in this field may be used.

For example, the catalyst composition may further include at least one of the following Chemical Formulae 7 to 12 as the cocatalyst.

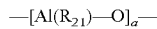 [Chemical Formula 7]

In the above Chemical Formula, each $R_{21}$ is independently a halogen radical; a hydrocarbyl radical having 1 to 20 carbon atoms; or a halogen substituted hydrocarbyl radical having 1 to 20 carbon atoms; and a is an integer of at least 2;

 [Chemical Formula 8]

In the above Chemical Formula, D is aluminum or boron; each $R_{22}$ is independently a halogen radical; a hydrocarbyl radical having 1 to 20 carbon atoms; or a halogen substituted hydrocarbyl radical having 1 to 20 carbon atoms;

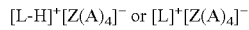 [Chemical Formula 9]

In the above Chemical Formula, L is a neutral or a cationic Lewis acid; H is a hydrogen atom; Z is an element in group 13; each A is independently aryl having 6 to 20 carbon atoms or alkyl having 1 to 20 carbon atoms, where at least one hydrogen atom may be substituted with a substituent; and the substituent is halogen, hydrocarbyl having 1 to 20 carbon atoms, alkoxy having 1 to 20 carbon atoms or aryloxy having 6 to 20 carbon atoms.

As a preparation method of the catalyst composition, a first preparation method including a step of obtaining a mixture by contacting the transition metal compound represented by the above Chemical Formula 1 with the compound represented by the above Chemical Formula 7 or 8; and a step of adding a compound represented by the above Chemical Formula 9 in the mixture is provided.

A second preparation method of the catalyst composition by contacting the transition metal compound represented by the above Chemical Formula 1 and the compound represented by the above Chemical Formula 9, is provided.

In the first method of the preparation methods of the catalyst composition, the molar ratio of the compound represented by the above Chemical Formula 7 or 8 with respect to the transition metal compound represented by the above Chemical Formula 1 is preferably from 1:2 to 1:5,000, more preferably, from 1:10 to 1:1,000, and most preferably, from 1:20 to 1:500.

Meanwhile, the molar ratio of the compound represented by the above Chemical Formula 9 with respect to the transition metal compound represented by the above Chemical Formula 1 is preferably from 1:1 to 1:25, more preferably, from 1:1 to 1:10, and most preferably, from 1:1 to 1:5.

In the case that the molar ratio of the compound represented by the above Chemical Formula 7 or 8 with respect to the transition metal compound represented by the above Chemical Formula 1 is less than 1:2, the amount of an alkylating agent is very small, and the alkylation of the metal compound may be incompletely performed, and in the case that the molar ratio exceeds 1:5,000, the alkylation of the metal compound may be performed, however a side reaction between the remaining alkylating agent and the activating agent of the above Chemical Formula 9 may be performed, and the activation of the alkylated metal compound may be incompletely performed. In addition, in the case that the molar ratio of the compound represented by the above Chemical Formula 9 with respect to the transition metal compound represented by the above Chemical Formula 1 is less than 1:1, the amount of the activating agent is relatively small, the activation of the metal compound may be incompletely performed, and the activity of the catalyst composition may be deteriorated, and in the case that the molar ratio exceeds 1:25, the activation of the metal compound may be completely performed, however the excessive activating agent remained may increase the production cost of the catalyst composition, or the purity of the polymer thus prepared may be deteriorated.

In the second method of the preparation methods of the catalyst composition, the molar ratio of the compound represented by the above Chemical Formula 9 with respect to the transition metal compound represented by the above Chemical Formula 1 is preferably from 1:1 to 1:500, more preferably, from 1:1 to 1:50, and most preferably, from 1:2 to 1:25. In the case that the molar ratio is less than 1:1, the amount of the activating agent is relatively small, and the activation of the catalyst composition may be deteriorated, and in the case that the molar ratio exceeds 1:500, the activation of the metal compound may be completely performed, however the excessive activating agent remained may increase the production cost of the catalyst composition, or the purity of the polymer thus prepared may be deteriorated.

As a reaction solvent used during the preparation of the composition, a hydrocarbon solvent such as pentane, hexane, heptane, etc, or an aromatic solvent such as benzene, toluene, etc. may be used, however the present invention is not limited thereto, and all solvents used in this field may be used.

In addition, the transition metal compound of the above Chemical Formula 1 and the cocatalyst may be used as a supported type by a support. Silica or alumina may be used as the support.

The compound represented by the above Chemical Formula 7 is not specifically limited only if alkylaluminoxane is used. Preferably, the compound includes methylaluminoxane, ethylaluminoxane, isobutylaluminoxane, butylaluminoxane, etc., and the methylaluminoxane is a particularly preferable compound.

The compound represented by the above Chemical Formula 8 is not specifically limited and preferably includes trimethylaluminum, triethylaluminum, triisobutylaluminum, tripropylaluminum, tributylaluminum, dimethylchloroaluminum, triisopropylaluminum, tri-s-butylaluminum, tricyclopentylaluminum, tripentylaluminum, triisopentylaluminum, trihexylaluminum, trioctylaluminum, ethyldimethylaluminum, methyldiethylaluminum, triphenylaluminum, tri-p-tolylaluminum, dimethylaluminummethoxide, dimethylaluminumethoxide, trimethylboron, triethylboron, triisobutylboron, tripropylboron, tributylboron, etc., and particularly preferable compound is selected from the trimethylaluminum, the triethylaluminum, and the triisobutylaluminum.

Examples of the compound represented by the above Chemical Formula 9 includes triethylammoniumtetraphenylboron, tributylammoniumtetraphenylboron, trimethylammoniumtetraphenylboron, tripropylammoniumtetraphenylboron, trimethylammoniumtetra(p-tolyl)boron, trimethylammoniumtetra(o,p-dimethylphenyl)boron, tributylammoniumtetra(p-trifluoromethylphenyl)boron, trimethylammoniumtetra(p-trifluoromethylphenyl)boron, tributylammoniumtetrapentafluorophenylboron, N,N-diethylaniliniumtetraphenylboron, N,N-diethylaniliniumtetrapentafluorophenylboron, diethylammoniumtetrapentafluorophenylboron, triphenylphosphoniumtetraphenylboron, trimethylphosphoniumtetraphenylboron, triethylammoniumtetraphenylaluminum, tributylammoniumtetraphenylaluminum, trimethylammoniumtetraphenylaluminum, tripropylammoniumtetraphenylaluminum, trimethylammoniumtetra(p-tolyl)aluminum, tripropylammoniumtetra(p-tolyl)aluminum, triethylammoniumtetra(o,p-dimethylphenyl)aluminum, tributylammoniumtetra(p-trifluoromethylphenyl)aluminum, trimethylammoniumtetra(p-trifluoromethylphenyl)aluminum, tributylammoniumtetrapentafluorophenylaluminum, N,N-diethylaniliniumtetraphenylaluminum, N,N-diethylaniliniumtetrapentafluorophenylaluminum, diethylammoniumtetrapentatetraphenylaluminum, triphenylphosphoniumtetraphenylaluminum, trimethylphosphoniumtetraphenylaluminum, tripropylammoniumtetra(p-tolyl)boron, triethylammoniumtetra(o,p-dimethylphenyl)boron, triphenylcarboniumtetra(p-trifluoromethylphenyl)boron, triphenylcarboniumtetrapentafluorophenylboron, etc.

A polyolefin homopolymer or copolymer may be prepared by contacting the catalyst composition including the transition metal compound of the above Chemical Formula 1; and at least one compound selected from the compounds represented by Chemical Formulae 7 to 9 with at least one olefin monomer.

The most preferable preparation process using the catalyst composition is a solution process. In the case that the composition is used together with an inorganic support such as silica, a slurry process or a gas phase process may be also applied.

In the preparation process, the activating catalyst composition may be inserted after being dissolved or diluted in an aliphatic hydrocarbon solvent having 5 to 12 carbon atoms such as pentane, hexane, heptane, nonane, decane and an isomer thereof, an aromatic hydrocarbon solvent such as toluene and benzene, or a hydrocarbon solvent substituted with a chlorine atom such as dichloromethane and chlorobenzene. The solvent may preferably be used after removing a small amount of water or air, which functions as a catalyst poison, by treating with a small amount of an alkylaluminum, and may be used by further using a cocatalyst.

The olefin monomer polymerizable using the metal compound and the cocatalyst may include ethylene, an alpha-olefin, a cyclic olefin, etc., and a diene olefin monomer, a triene olefin monomer, etc. having at least two double bonds may also be polymerized. Particular examples of the monomer may include ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, 1-icocene, norbornene, norbornadiene, ethylidenenorbornene, phenylnorbornene, vinylnorbornene, dicyclopentadiene, 1,4-butadiene, 1,5-pentadiene, 1,6-hexadiene, styrene, alpha-methylstyrene, divinylbenzene, 3-chloromethylstyrene, etc. A mixture of at least two of these monomers may be copolymerized.

Particularly, in the preparation method of the present invention using the catalyst composition, a copolymer having high molecular weight and a polymer density of less than or equal to 0.91 g/cc may be prepared in a copolymerization reaction of ethylene with a monomer having large steric hindrance such as 1-octene at a high reaction temperature greater than or equal to 90° C.

According to an aspect, the polymer prepared by the preparation method of the present invention has a density of less than 0.91 g/cc.

According to another aspect, the polymer prepared by the preparation method of the present invention has a density of less than 0.89 g/cc.

According to an aspect, the polymer prepared by the preparation method of the present invention has a density of less than or equal to 0.885 g/cc.

According to an aspect, the polymer prepared by the preparation method of the present invention has a Tc of less than or equal to 75° C.

According to an aspect, the polymer prepared by the preparation method of the present invention has a Tm of less than or equal to 95° C.

According to an aspect, the polymer prepared by the preparation method of the present invention has a Tm of less than or equal to 91° C.

According to an aspect, the polymer prepared by the preparation method of the present invention has a Tm of less than 87° C.

According to an aspect, the polymer prepared by the preparation method of the present invention has a Mw of greater than or equal to 100,000.

According to another aspect, the polymer prepared by the preparation method of the present invention has a Mw of 100,000 to 1,000,000.

According to an aspect, the polymer prepared by the preparation method of the present invention has a MWD of less than or equal to 3.

According to another aspect, the polymer prepared by the preparation method of the present invention has a MWD of 1 to 3.

According to another aspect, the polymer prepared by the preparation method of the present invention has a MWD of 1.5 to 2.9.

According to another aspect, the polymer prepared by the preparation method of the present invention has a MWD of 2 to 2.85

According to an aspect, the polymer according to the present invention has a MWD of 1 to 3, a Mw of 100,000 to 1,000,000, and a density of less than 0.91 g/cc.

MODE FOR CARRYING OUT THE INVENTION

Hereinafter, the present invention will be explained more particularly referring to the following embodiments. The embodiments are for assisting the understanding of the present invention, and the scope of the present invention is not limited thereto.

Organic reagents and solvents were purchased from Aldrich Co. and used after purifying by a standard method unless otherwise mentioned. In all steps of syntheses, air and humidity were blocked to increase the reproducibility of experiments.

Synthesis of Transition Metal Compound

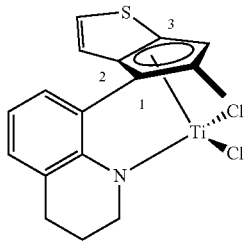

Synthesis of Ketone Compound

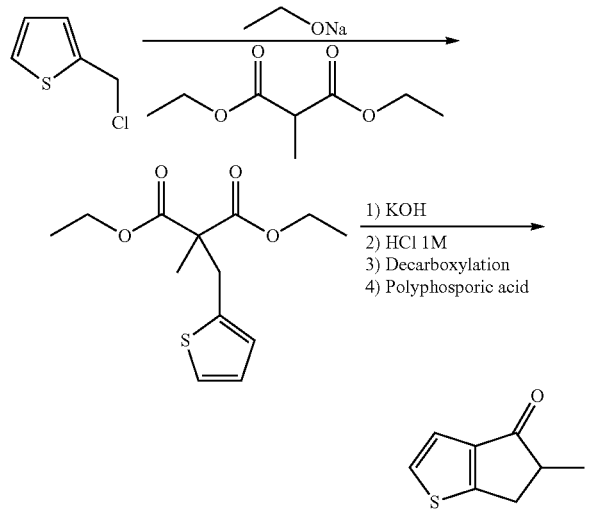

The synthesis was performed according to the method described in a document [Ryabov et al. *Organometallics*, 2002, 21, 14, 2842-2853].

$^1$H NMR (CDCl$_3$): δ1.35 (d, 3H, CH$_3$), 2.78 (dd, 1H), 3.05 (m, 1H, (CH$_2$)$_2$), 3.43 (dd, 1H), 1.91 (m, 6H, Cp-CH$_3$), 7.14 (d, 1H), 7.34 (d, 1H) ppm Synthesis of Ligand

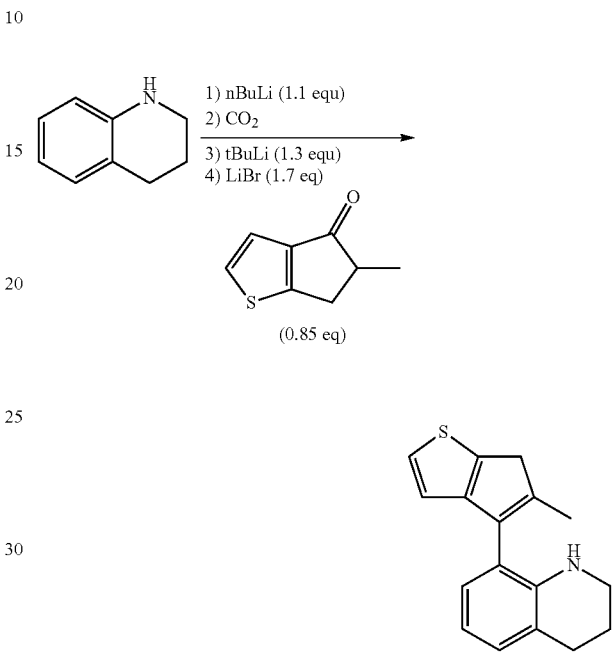

To 1,2,3,4-tetrahydroquinoline (560 mg, 4.2 mmol) dissolved in 10 mL of ether, n-butyllithium (4.6 mmol, 1.1 eq.) was slowly added dropwisely at −40° C. The temperature was slowly elevated to room temperature, followed by stirring at room temperature for 4 hours. The temperature was decreased to −40° C. again, and CO$_2$(g) was injected thereto, followed by maintaining the reaction at a low temperature for 0.5 hours. The temperature was slowly elevated, and remaining CO$_2$(g) was removed through a bubbler. THF (4.6 mmol, 0.37 ml) and tBuLi (4.6 mmol) were inserted at −20° C., followed by aging at a low temperature of −20° C. for 2 hours. The above ketone compound (540 mg, 3.57 mmol) was dissolved in a diethyl ether solution and slowly added dropwisely. After stirring for 12 hours at room temperature, 10 mL of water was added and hydrochloric acid (2N, 20 mL) was added, followed by stirring for 2 minutes. An organic solvent was extracted and neutralized with a NaHCO$_3$ aqueous solution. The organic solvent was extracted, and water was removed with MgSO$_4$. Through silica gel column chromatography, a yellow oil (230 mg, 24% yield) was obtained.

$^1$H NMR (C$_6$D$_6$): δ 1.83 (s, 3H, CH$_3$), 2.40~2.38 (m, 4H, Cp-H quinoline-CH$_2$), 2.62~2.60 (m, 2H, quinoline-CH$_2$), 2.61~2.59 (m, 2H, quinoline-NCH$_2$), 2.81~2.77 (d, 2H, quinoline-NCH$_2$), 2.97~2.94 (d, 2H, quinoline-NCH$_2$), 3.69 (broad, 1H, N—H), 6.77~6.74 (t, 1H, aromatic), 6.83~6.82 (s, 1H, aromatic), 6.93~6.92 (s, 1H, aromatic), 7.11~7.10 (s, 1H, aromatic), 7.30 (s, 1H, aromatic), 7.72~7.70 (d, 1H, aromatic) ppm

Synthesis of Transition Metal Compound

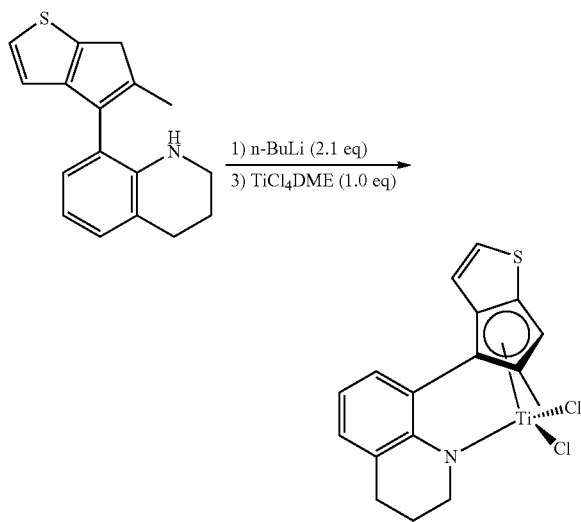

N-butyllithium (1.15 mmol, 2.1 eq.) was slowly added to the above ligand (147 mg, 0.55 mmol) at 20° C. The formation of a yellow slurry was observed, and the temperature was slowly elevated to room temperature, followed by stirring at room temperature for 12 hours.

TiCl$_4$DME (154 mg, 0.55 mmol, 1.0 eq.) was added dropwisely, followed by stirring at room temperature for 12 hours. After removing solvents, the remaining product was extracted with toluene to obtain a red solid (63 mg, 30% yield).

$^1$H NMR (C$_6$D$_6$): δ 1.46~1.467 (t, 2H, quinoline-NCH$_2$), 1.81 (s, 3H, Cp-CH$_3$), 2.10~2.07 (t, 2H, quinoline-NCH$_2$), 4.45~4.41 (m, 2H, N—CH$_2$), 4.53~4.50 (m, 2H, N—CH$_2$), 6.00 (Cp, 1H), 6.38~6.37 (d, 1H, aromatic) 6.70~6.69 (d, 1H, aromatic) 6.85~6.83 (m, 2H, aromatic) 6.98~6.96 (d, 1H, aromatic) ppm

Preparation Example of Polymer

Examples 1 and 2 and Comparative Examples 1 and 2

A hexane solvent (1.0 L) and 1-octene (0.84 M) were inserted in a 2 L autoclave reactor, followed by pre-heating the reactor to 120° C. At the same time, the pressure of the reactor was filled with ethylene (35 bar) in advance. A compound (2.0 µmol) in the first column in the following Table 1, which is treated with a triisobutyl aluminum compound and a dimethylanilinium tetrakis(pentafluorophenyl)borate cocatalyst (20 µmol) were inserted in the reactor one by one while pressurizing using argon with high pressure (molar ratio of Al:Ti=10:1). Then, a copolymerization reaction was performed for 8 minutes. After that, the remaining ethylene gas was exhausted, and a polymer solution was added to an excessive amount of ethanol to induce precipitation. The precipitated polymer was washed with ethanol and acetone twice or three times, respectively, and dried in a vacuum oven at 80° C. for more than 12 hours. Then, physical properties were evaluated.

Evaluation of Physical Properties (Weight, Activity, Melting Index, Melting Point, Density)

Melt index (MI) of a polymer was measured according to ASTM D-1238 (condition E, 190° C., 2.16 kg load). The melting point (Tm) of the polymer was obtained by using a differential scanning calorimeter 2920 (DSC) manufactured by TA Co. That is, the temperature was elevated to 200° C., maintained for 5 minutes, decreased to 30° C. and elevated again, and the apex of a DSC curve was measured as the melting point. In this case, the elevating rate and the decreasing rate of the temperature was 10° C./min, and the melting point was obtained during the second elevation of the temperature. In addition, the density of the polymer was measured by manufacturing a sheet having a thickness of 3 mm and a radius of 2 cm by using a press mold at 180° C. of a sample treated with an antioxidant (1,000 ppm), cooling at a rate of 10° C./min, and measuring using a Mettler balance.

The physical properties of the polymers prepared in the above examples and comparative examples are illustrated in the following Table 1.

TABLE 1

| Cat | C8 (mL) | Yield (g) | MI$^{2.16}$ | Density (g/mL) | Tc (° C.) | Tm (° C.) | MW | MWD |
|---|---|---|---|---|---|---|---|---|
| Comparative Example 1 | 210 | 71.1 | 0.55 | 0.873 | 48.5 | 63.0 | 152197 | 2.34 |
| Comparative Example 2 | 210 | 84 | 0.18 | 0.890 | (39.1), 69.4 | 87.0 | 155195 | 2.67 |
| Example 1 | 210 | 19.6 | 0.97 | 0.871 | 38.7, (72.9) | 57.5, (117.7) | 151076 | 2.27 |
| Example 2 | 280 | 20.2 | 1.05 | 0.863 | 13.8, (73.1) | 41.0, (118.5) | 157642 | 2.54 |

Polymerization conditions: hexane (1.0 L), ethylene (35 bar), 120° C., Tibal, Ti catalyst (2.0 µmol), cocatalyst AB 10 eq. (20 µmol)

Kind of catalyst:   Examples 1 & 2     Comparative Example 1

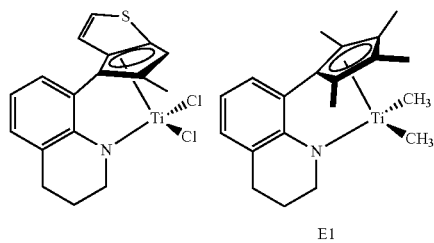

E1

TABLE 1-continued

| Cat | C8 (mL) | Yield (g) | MI[2.16] | Density (g/mL) | Tc (° C.) | Tm (° C.) | MW | MWD |
|---|---|---|---|---|---|---|---|---|

Comparative Example 2

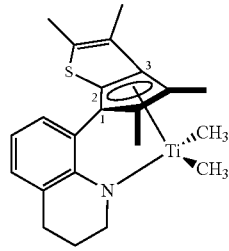

Catalyst of Comparative Example 1: prepared by WO2008/084931A1
Catalyst of Comparative Example 2: prepared by KR 10-0986301
MI[2.16]: Melt Index
Tc: crystallization point (° C.)
Tm: melting point (° C.)

INDUSTRIAL APPLICABILITY

The transition metal compound according to an embodiment of the present invention has good copolymerization properties, and a polymer having a low density may be prepared using thereof. Thus, a copolymer having various uses may be prepared.

The invention claimed is:
1. A transition metal compound of the following Chemical Formula 2:

[Chemical Formula 2]

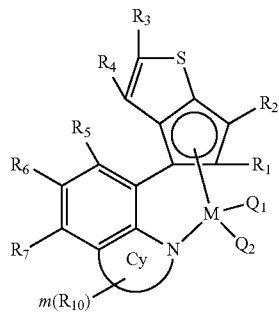

in the above Chemical Formula 2,
M is a transition metal in group 4,
$Q_1$ and $Q_2$ are the same or different and each independently hydrogen; halogen; alkyl having 1 to 20 carbon atoms; alkenyl having 2 to 20 carbon atoms; aryl having 6 to 20 carbon atoms; alkylaryl having 6 to 20 carbon atoms; arylalkyl having 7 to 20 carbon atoms; alkylamido having 1 to 20 carbon atoms; arylamido having 6 to 20 carbon atoms; or alkylidene having 1 to 20 carbon atoms,
$R_1$ to $R_4$ are the same or different and each independently hydrogen; silyl; alkyl having 1 to 20 carbon atoms; alkenyl having 2 to 20 carbon atoms; aryl having 6 to 20 carbon atoms; alkylaryl having 7 to 20 carbon atoms; arylalkyl having 7 to 20 carbon atoms; a metalloid radical of a metal in group 14, substituted with hydrocarbyl having 1 to 20 carbon atoms; $R_1$ and $R_2$ are optionally connected to each other, or $R_3$ and $R_4$ are optionally connected to each other to form an aliphatic ring having 5 to 20 carbon atoms or an aromatic ring having 6 to 20 carbon atoms; the aliphatic ring or the aromatic ring is optionally substituted with halogen, alkyl having 1 to 20 carbon atoms, alkenyl having 2 to 20 carbon atoms, or aryl having 6 to 20 carbon atoms, and
$R_5$ to $R_7$ are the same or different and independently hydrogen; alkyl having 1 to 20 carbon atoms; alkenyl having 2 to 20 carbon atoms; aryl having 6 to 20 carbon atoms; alkylaryl having 7 to 20 carbon atoms; arylalkyl having 7 to 20 carbon atoms; at least two of $R_5$ to $R_7$ are optionally connected to each other to form an aliphatic ring having 5 to 20 carbon atoms or an aromatic ring having 6 to 20 carbon atoms; the aliphatic ring or the aromatic ring is optionally substituted with halogen, alkyl having 1 to 20 carbon atoms, alkenyl having 2 to 20 carbon atoms, or aryl having 6 to 20 carbon atoms,
Cy is a five-membered or six-membered aliphatic ring,
each $R_{10}$ is independently hydrogen; alkyl having 1 to 20 carbon atoms; alkenyl having 2 to 20 carbon atoms; aryl having 6 to 20 carbon atoms; alkylaryl having 7 to 20 carbon atoms; or arylalkyl having 7 to 20 carbon atoms,
m is an integer from 1 to 4 when Cy is the five-membered aliphatic ring, and an integer from 1 to 6 when Cy is the six-membered aliphatic ring.

2. The transition metal compound of claim 1, wherein $R_1$ and $R_2$ are independently hydrogen or alkyl having 1 to 20 carbon atoms.

3. The transition metal compound of claim 1, wherein the above Chemical Formula 2 is represented by the following Chemical Formula 3 or Chemical Formula 4:

[Chemical Formula 3]

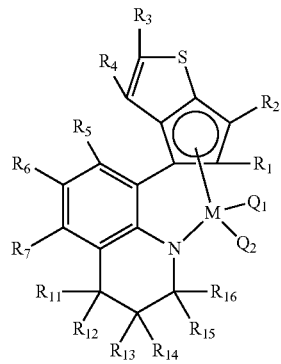

in the above Chemical Formula 3,
$R_{11}$ to $R_{16}$ are each independently hydrogen; alkyl having 1 to 20 carbon atoms; alkenyl having 2 to 20 carbon atoms; aryl having 6 to 20 carbon atoms; alkylaryl having 7 to 20 carbon atoms; or arylalkyl having 7 to 20 carbon atoms, and the remaining substituents are the same as defined in Chemical Formula 2,

[Chemical Formula 4]

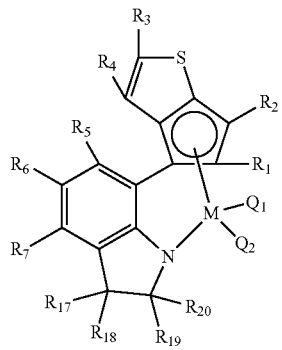

in the above Chemical Formula 4, $R_{17}$ to $R_{20}$ are each independently hydrogen; alkyl having 1 to 20 carbon atoms; alkenyl having 2 to 20 carbon atoms; aryl having 6 to 20 carbon atoms; alkylaryl having 7 to 20 carbon atoms; or arylalkyl having 7 to 20 carbon atoms, and the remaining substituents are the same as defined in Chemical Formula 2.

4. The transition metal compound of claim 3, wherein $R_1$, $R_2$, $R_{16}$ and $R_{20}$ are independently hydrogen or alkyl having 1 to 20 carbon atoms.

5. The transition metal compound of claim 1, wherein the above Chemical Formula 2 is represented by the following Chemical Formula 5 or 6

[Chemical Formula 5]

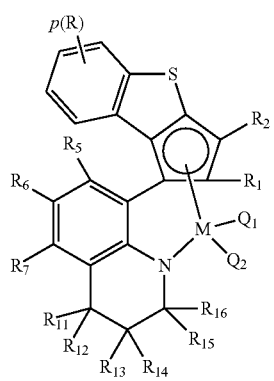

in the above Chemical Formula 5,

R and $R_{11}$ to $R_{16}$ are each independently hydrogen; alkyl having 1 to 20 carbon atoms; alkenyl having 2 to 20 carbon atoms; aryl having 6 to 20 carbon atoms; alkylaryl having 7 to 20 carbon atoms; or arylalkyl having 7 to 20 carbon atoms, p is an integer from 1 to 4, and the remaining substituents are the same as defined in Chemical Formula 2,

[Chemical Formula 6]

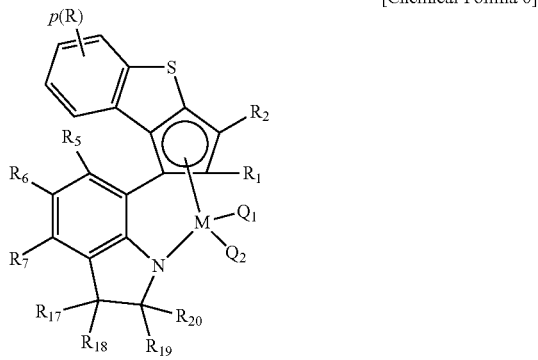

in the above Chemical Formula 6,

R and $R_{17}$ to $R_{20}$ are each independently hydrogen; alkyl having 1 to 20 carbon atoms; alkenyl having 2 to 20 carbon atoms; aryl having 6 to 20 carbon atoms; alkylaryl having 7 to 20 carbon atoms; or arylalkyl having 7 to 20 carbon atoms, p is an integer from 1 to 4, and the remaining substituents are the same as defined in Chemical Formula 2.

6. The transition metal compound of claim 5, wherein $R_1$, $R_2$, $R_{16}$ and $R_{20}$ are independently hydrogen or alkyl having 1 to 20 carbon atoms.

7. The transition metal compound of claim 1, wherein M is Ti, Hf or Zr.

8. The transition metal compound of claim 1, wherein the compound of the above Chemical Formula 2 is one selected from compounds represented in the following Chemical formulae or a mixture of at least two thereof:

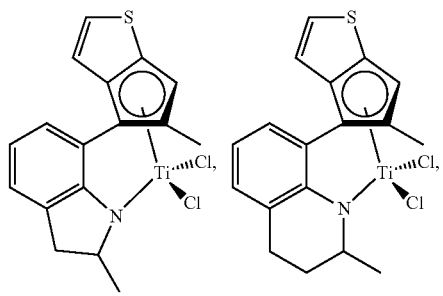

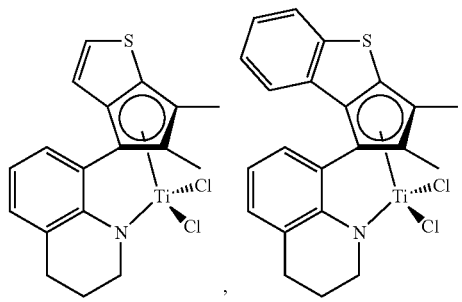

-continued

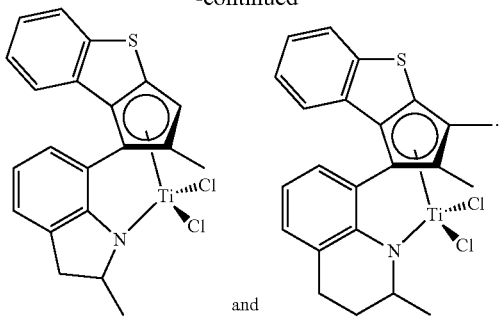

and

9. A catalyst composition comprising the transition metal compound according to claim 1.

10. The catalyst composition of claim 9, which further comprises at least one kind of a cocatalyst.

11. The catalyst composition of claim 10, wherein the cocatalyst comprises at least one selected from the following Chemical Formulae 7 to 9:

$$—[Al(R_{22})—O]_a—$$ [Chemical Formula 7]

in the above Chemical Formula 7, each $R_{22}$ is independently a halogen radical; a hydrocarbyl radical having 1 to 20 carbon atoms; or a halogen substituted hydrocarbyl radical having 1 to 20 carbon atoms; and a is an integer of at least 2;

$$D(R_{22})_3$$ [Chemical Formula 8]

in the above Chemical Formula 8, D is aluminum or boron; each $R_{22}$ is independently the same as described above;

$$[L-H]^+[Z(A)_4]^- \text{ or } [L]^+[Z(A)_4]^-$$ [Chemical Formula 9]

in the above Chemical Formula 9, L is a neutral or a cationic Lewis acid; H is a hydrogen atom; Z is an element in group 13; each A is independently aryl having 6 to 20 carbon atoms or alkyl having 1 to 20 carbon atoms, where at least one hydrogen atom is optionally independently be substituted with a substituent; and the substituent is halogen, hydrocarbyl having 1 to 20 carbon atoms, alkoxy having 1 to 20 carbon atoms or aryloxy having 6 to 20 carbon atoms.

12. The catalyst composition of claim 9, which further comprises a reaction solvent.

13. A supported catalyst in which the catalyst composition according to claim 9 is supported by a support.

14. A preparation method of a polymer using the catalyst composition according to claim 9.

15. The preparation method of a polymer of claim 14, wherein the polymer is a homopolymer or a copolymer of a polyolefin.

16. A preparation method of a polymer using the supported catalyst according to claim 13.

17. The preparation method of a polymer of claim 16, wherein the polymer is a homopolymer or a copolymer of a polyolefin.

* * * * *